United States Patent [19]

Yamamoto

[11] Patent Number: 4,968,828
[45] Date of Patent: Nov. 6, 1990

[54] FLUORINE-CONTAINING ORGANOSILICON COMPOUND

[75] Inventor: Yasushi Yamamoto, Takasaki, Japan

[73] Assignee: Shin-Etsu Chemical Co., Ltd., Tokyo, Japan

[21] Appl. No.: 424,533

[22] Filed: Oct. 20, 1989

[30] Foreign Application Priority Data

Oct. 21, 1988 [JP] Japan .................. 63-265634

[51] Int. Cl.$^5$ .................. C07F 7/08; C07F 7/18
[52] U.S. Cl. .................. 556/448; 556/451
[58] Field of Search .................. 556/448, 451

[56] References Cited

U.S. PATENT DOCUMENTS

| | | | |
|---|---|---|---|
| Re. 31,324 | 7/1983 | Apotheker | 556/468 X |
| 3,331,813 | 7/1967 | Pittman et al. | 556/468 X |
| 3,334,123 | 8/1967 | Culpepper | 556/448 |
| 3,422,131 | 1/1969 | Pittman et al. | 556/448 |
| 4,227,172 | 2/1988 | Yamamoto et al. | 556/451 X |
| 4,489,201 | 12/1989 | Vou Au et al. | 556/448 X |
| 4,927,950 | 5/1990 | Hisamoto et al. | 556/468 X |

Primary Examiner—Paul F. Shaver
Attorney, Agent, or Firm—Foley & Lardner, Schwartz, Jeffery, Schwaab, Mack, Blumenthal & Evans

[57] ABSTRACT

A fluorine-containing organosilicon compound represented by the following general formula:

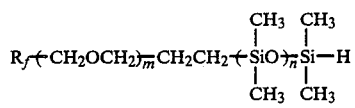

wherein $R_f$ represents a perfluoroalkyl group or a perfluoroalkyl ether group, and m and n are each an integer of 0 or 1. This fluorine-containing organic silicon compound is useful as a modifier for improving properties of various materials, such as heat resistance, chemical resistance and surface properties.

5 Claims, 9 Drawing Sheets

FLUORINE-CONTAINING ORGANOSILICON COMPOUND

BACKGROUND OF THE INVENTION

1. Field of the Invention

This invention relates to a novel fluorine-containing organosilicon compound.

2. Description of the Prior Art

Introduction of a fluorine-containing group into an organic compound has been conducted in order to improve various properties of the organic compound or materials containing the organic compound, such as heat resistance, chemical resistance and surface properties. Heretofore, in order to introduce a fluorine-containing organic group into an organic compound, there is used a method in which the fluorine-containing group is bonded to the organic compound through a known bond such as an ether, amine, sulfide, urethane or ester bond.

However, the known fluorine-containing organic compound obtained by the above method generally have poor compatibility to general materials. Where a fluorine-containing organic group is introduced into an organic compound through ether bonding or amine bonding according to the above method, it is difficult to efficiently introduce the fluorine-containing organic groups. Moreover, an organic compound into which is introduced a fluorine-containing organic group through urethane bonding according to the above method has poor heat resistance.

SUMMARY OF THE INVENTION

Accordingly, it is an object of the present invention to provide a novel fluorine-containing organosilicon compound having good compatibility with various materials and useful as a modifier for improving heat resistance, chemical resistance or surface properties of various materials.

Thus, according to the present invention, there is provided a fluorine-containing organosilicon compound represented by the following general formula (I):

$$R_f\text{--}(CH_2OCH_2)_{\overline{m}}CH_2CH_2\text{--}(SiO)_{\overline{n}}\underset{\underset{CH_3}{|}}{\overset{\overset{CH_3}{|}}{Si}}\text{--}H \quad \quad (I)$$
(with $CH_3$ groups on the middle Si)

wherein $R_f$ is a perfluoroalkyl group or a perfluoroalkyl ether group, and m and n are each an integer of 0 or 1.

DETAILED DESCRIPTION OF THE INVENTION

Figure 1:
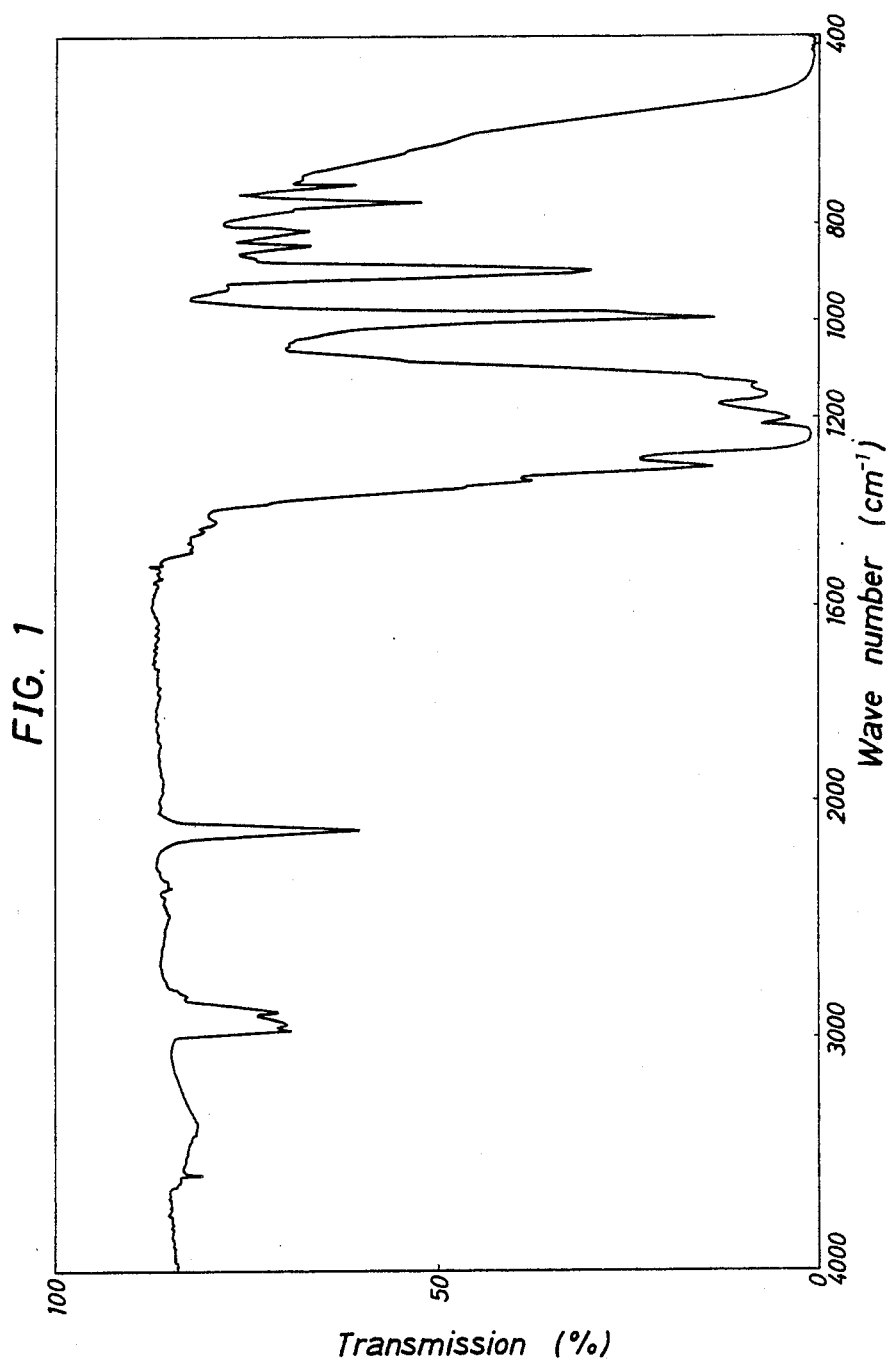
FIGS. 1 to 9 show infrared absorption spectra of fluorine-containing organosilicon compounds of the present invention obtained in Examples 1 to 3 and 5 to 10, respectively.

In the general formula (I), the group $R_f$ is a Perfluoroalkyl group or a perfluoroalkylether group.

The perfluoroalkyl group may be either of a linear one and a branched one, but the branched one is preferable from a view point of synthesis.

The perfluoroalkyl group is preferably ones having 4 to 10 carbons. Specific examples such preferred perfluoroalkyl groups include a nonafluorobutyl group, an undecafluoropentyl group, a tridecafluorohexyl group, a pentadecafluoroheptyl group, a heptadeafluorooctyl group, a nonadecafluorononyl group and a heneicosafluorodecyl group. Typical examples of these are ones having 4, 6 or 8 carbons.

Preferred perfluoroalkylether groups have 5 to 14 carbons; especially preferred is the one represented by the following formula (II):

$$F(CFCF_2O)_s\underset{\underset{CF_3}{|}}{CF}\text{--} \quad \quad (II)$$
(with $CF_3$ on the left CF)

wherein s is an integer of 1 to 4.

Such a perfluoroalkylether group can be formed by oligomerization of, for example, hexafluoropropylene oxide.

In the above general formula (I), m is an integer of 0 or 1. Where the group $R_f$ is a perfluoroalkyl group, m is preferably 0. Namely, the fluorine-containing organosilicon compound in this case is represented by the following formula (Ia):

$$C_pF_{2p+1}\text{--}CH_2CH_2\text{--}(SiO)_{\overline{n}}\underset{\underset{CH_3}{|}}{\overset{\overset{CH_3}{|}}{Si}}\text{--}H \quad \quad (Ia)$$

wherein p is an integer of 4 to 10.

On the other hand, where the group $R_f$ is a perfluoroalkylether group, m is preferably 1. The fluorine-containing organosilicon compound in this case is represented by the following formula (Ib):

$$F(CFCF_2O)_s\underset{\underset{CF_3}{|}}{CF}\text{--}CH_2OCH_2\text{--}CH_2CH_2\text{--}(SiO)_{\overline{n}}\underset{\underset{CH_3}{|}}{\overset{\overset{CH_3}{|}}{Si}}\text{--}H \quad \quad (Ib)$$

Preparation of the fluorine-containing organosilicon compound

Preparation methods of the novel fluorine-containing organosilicon compound of the present invention will be described below in respect of the case where n is 0 and the case where n is 1.

First, in the case where n is 0, used as a starting material is a chlorosilane having a molecular structure corresponding to a desired fluorine-containing organosilicon compound. Namely, the fluorine-containing organosilicon compound is prepared by reduction of the chlorosilane with a metal hydride as shown in the reaction equation (A) below in accordance with a method reported in W.H. Hebergall, O.H. Johnson, J.Am. Chem. Soc., 71, 4022 (1949).

$$R_fCH_2O(CH_2)_3\underset{\underset{CH_3}{|}}{\overset{\overset{CH_3}{|}}{Si}}\text{--}Cl \xrightarrow{\text{metal hydride}} R_fCH_2O(CH_2)_3\underset{\underset{CH_3}{|}}{\overset{\overset{CH_3}{|}}{Si}}\text{--}H$$

Examples of the metal hydride used as a reducing agent in the reaction include LiAlH$_4$, Al(BH$_4$)$_3$ and LiH. Preferred solvents to be used for the reaction include, for example, tetrahydrofuran and dithyl ether, and mixed solvents containing at least one of these and a further solvent added as required, for example, other ether solvent such as dioxane, dibutyl ether and diisoproplyls ether, and hydrocarbon solvents such as n hexane, Cyclohexane, benzene, toluene and xylene.

Meanwhile, since the reducing power of the metal hydride used is restricted by kinds of a solvent employed, it is preferable to select the solvent suitably depending on the kind of the metal hydride employed. Typical combinations of the reducing agent and the solvent include for example, the combination of LiAlH. as the reducing agent and tetrahydrofuran as the solvent. The reducing agent is present typically in an amount of 1 to 2 moles in terms of hydride per mole of the chlorosilane. The reaction temperature is typically in the range of from 0 to 70 C.

The chlorosilane, the starting material of the reaction, can be obtained by a method reported in G.E. Berendsen et al., Anal. Chem. 52,1990 (1980) and Japanese Pre-examination Patent Publication (KOKAI) No. 255288/1983.

Secondly, the embodiment of the organosilicon compound of the present invention where n is 1 in the general formula (I), i.e., a disiloxane compound, can be prepared by a publicly known method. For example, as shown in the reaction equations below, the preparation can be carried out by (I) a method [Equation (B)]in which a partial addition reaction of 1,1,3,3-tetramethyl-disiloxane with an olefin substituted with a perfluoro group is used, or (2) a method [Equation (C)]in which an equilibration reaction of two kinds of disiloxane is used.

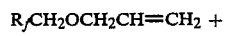

(III)

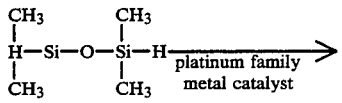

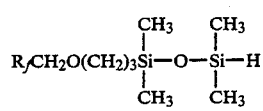

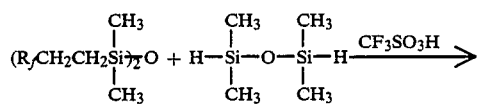

(IV)

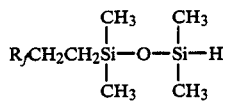

In these methods (1) and (2), 1,1,3,3-tetramethyldisiloxane is used excessively. Normally. it is used in an amount of 1 to 10 moles per mole of the fluorine-containing compound represented by the above formula (III) or (IV). The catalyst which may be used in the reaction (C) is not limited to CF,SO,H, and include, for example, sulfuric acid, phosphoric acid and hydrochloric acid. The reactions (C) and (D) are carried out typically at a temperature in the range of from room temperature to 80° C. Uses The novel fluorine-containing organosilicon compound of the present invention has a good compatibility with various materials in itself, and also excellent in properties, such as heat resistance, chemical resistance and surface properties. Therefore, it can be effectively used as a modifier for improving the above properties of materials such as various silicone resins by blending or reacting it with the material.

Also, it is possible to prepare a fluorine-containing silicone resin excellent in the above properties by applying known methods such as condensation using the fluorine-containing organosilicon compound of this invention as a starting material.

EXAMPLE 1

2.1g (0.055 mole) of lithium aluminum hydride and 100ml of tetrahydrofuran were charged into a 500ml four-neck flask, and then the gas inside was replaced with nitrogen gas. Into the reaction mixture was added dropwise 157g (0.2 mole) of 6,9,12-tris(trifluoromethyl)6,8,8,9,11,11,12,14,14,15,15,16,16,16-tetradecafluoro-4,7, 10, 13-tetraoxahexadecyldimentylchlorosilane at a temperature ranging from room temperature to 50° C. over 1 hour, and thereafter reaction was conducted at 40 to 50° C. for 2 hours. After the reaction, 10ml of methyl acetate was added, and the reaction mixture was treated at 40 to 50° C. for 30 minutes, thereby lithium aluminum hydride in excess remaining in the reaction mixture being decomposed. Subsequently, 150ml of water and 150ml of 3% hydrochloric acid were added, and the .reaction mixture was treated therewith. Thereafter, an organic layer in the flask was washed with a saturated aqueous salt cake solution three times, then dried, and distilled under vacuum to give 126g of a fraction of 97 to 98° C./3 mmHg.

The fraction obtained was subjected to elemental analysis and measurements of molecular weight by GC-MS analysis, infrared absorption spectrum and $^1$H-NMR spectrum. The following results were obtained.

Elemental analysis:

| | Elemental analysis: | | |
|---|---|---|---|
| | C | H | Si |
| Calculated* | 27.3 | 2.0 | 3.8 |
| Found | 27.1 | 1.8 | 3.9 |

(*Calculated as $C_{17}H_{15}F_{23}O_4Si$)

GC-MS analysis:

The molecular weight was determined to be 748. Infrared absorption spectrum: Shown in FIG. 1. A characteristic absorption peak due to Si-H bonds was recognized at a wave number of 2,125cm$^{-1}$. $^1$H-NMR spectrum internal standard: benzene, δ: a3.74 to 4.17ppm (d, 2H, <CF—CH$_2$O), 3.30 to 3.67ppm (t, 2H, —O—CH$_2$—C), 1.30 to 1.97ppm (m, 2H, —O—C—CH$_2$—C), 0.40 to 0.87ppm (m, 2H, —C—CH$_2$Si—), 0.24 to −0.13ppm (d, 6H, Si—CH$_3$), 3.74 to 4.17ppm (m, 1H, Si-H), From the above results, the compound obtained was identified as 6,9,12-tris(trifluoromethyl)-6,8,8,9,11,-11,12,14,14,15,15,16,16,16-tetradecafluoro-4,7,10,13tetraoxa represented by the following formula, and its yield was found to be 84%.

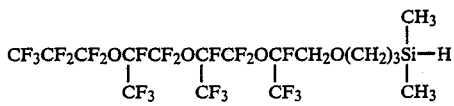

EXAMPLE 2

In the same manner as in Example 1, 93g (0.15 mole) of 6,9-bis(trifluoromethyl)-6,8,8,9,11,11,12,12,-13,13,13-undecafluoro-4,7,10-trioxatridecyldimethylchlorosilane was reacted with 1.52g (0.04 mole) of lithium aluminum hydride, and the reaction mixture obtained was distilled under vacuum to give 72g of a fraction with a boiling point of 80 to 81° C./6 mmHg.

The fraction obtained was subjected to elemental analysis, measurement of molecular weight by GC-MS analysis, and measurement of infrared absorption spectrum and $^1$H-NMR spectrum; the following results were thereby obtained.

| | Elemental analysis: | | |
|---|---|---|---|
| | C | H | Si |
| Calculated* | 28.9 | 2.6 | 4.8 |
| Found | 29.0 | 2.5 | 4.9 |

(*Calculated as $C_{14}H_{15}F_{17}O_3Si$)

Figure 2:
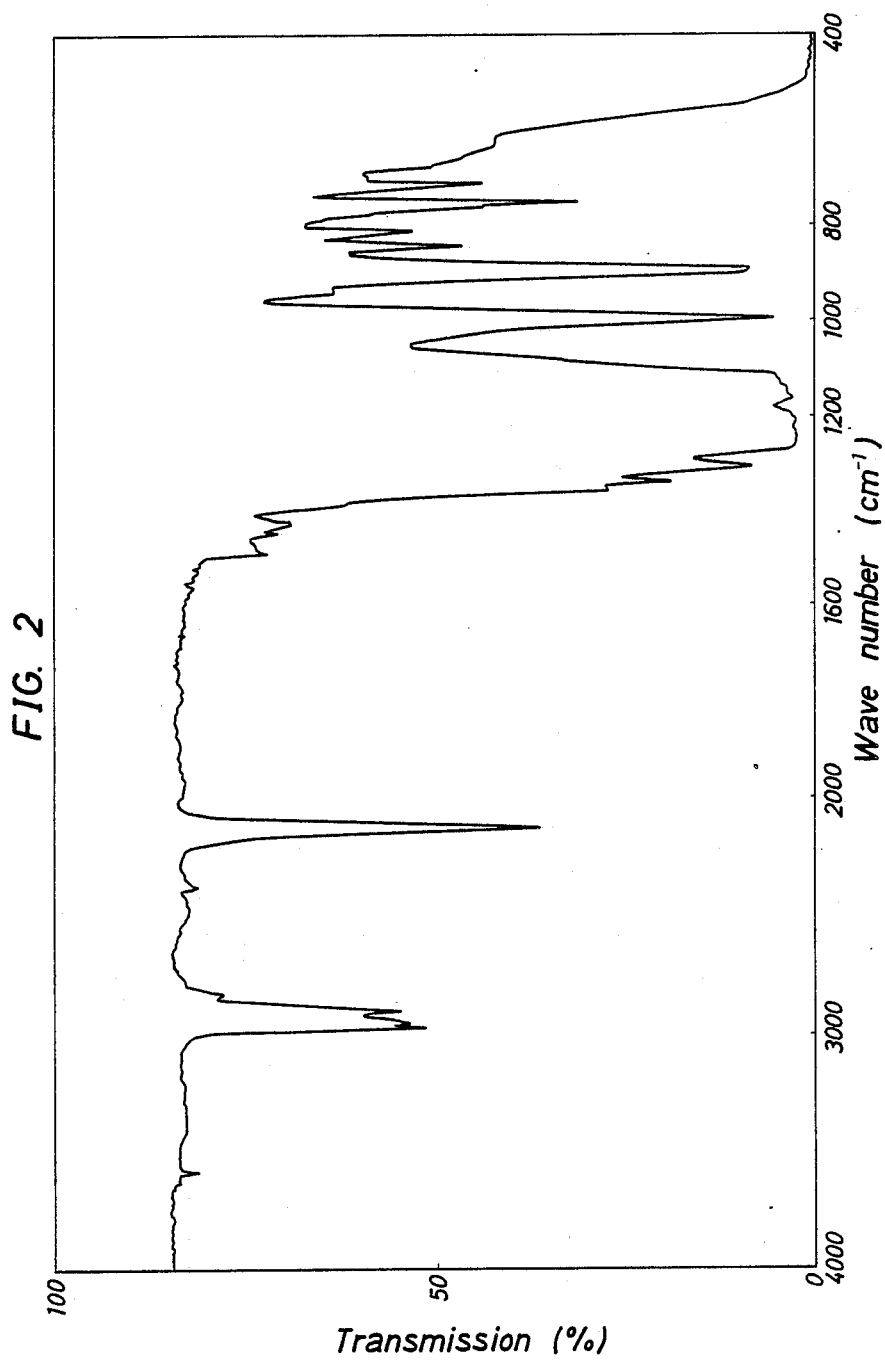

GC-MS analysis:

The molecular weight was determined to be 582. Infrared absorption spectrum: Shown in FIG. 2. A characteristic absorption peak due to Si-H was recognized at a wave number of 2,125cm$^{-1}$.

$^1$H-NMR spectrum:

internal standard: benzene.

δ: 3.70 to 4.20ppm (d, 2H, >CF—CH$_2$O),
3.30 to 3.66ppm (t, 2H, —O—CH$_2$—C),
1 30 to 1.97ppm (m, 2H, —O—C—CH$_2$—C),
0.40 to 0.87ppm (m, 2H, —C—CH$_2$Si—),
0 27 to −0.13ppm (d. 6H, Si—CH$_3$),
3.70 to 4.20ppm (m, 1H, Si—H), From the above results, the compound obtained was identified as 6,9-bis(trifluoromethyl)-6,8,8,9,11,11,-12,12,13,13,13-undecafluoro-4,7,10-trioxatridecyldimethylsila represented by the formula below, and its yield was calculated to be 82%.

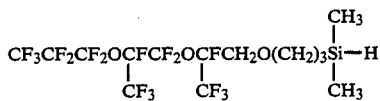

EXAMPLE 3

Procedure in Example was repeated, except that 68g (0.15 mole) of 6-trifluoromethyl-6,8,8,9,9,10,10,10-octafluoro-4,7-dioxadecyldimethylchlorosilane was used in place of the fluorine-containing silane used in Example 1; 47g of a fraction with a boiling point of 66 to 67° C./9 mmHg was obtained.

The fraction obtained was subjected to elemental analysis, measurement to molecular weight by GC-MS analysis, and measurement of infrared absorption spectrum and $^1$H-NMR spectrum, and the following results were obtained.

| | Elemental analysis: | | |
|---|---|---|---|
| | C | H | Si |
| Calculated* | 31.7 | 3.6 | 6.8 |
| Found | 31.5 | 3.7 | 6.7 |

(*Calculated as $C_{11}H_{15}F_{11}O_2Si$)

GC-MS analysis:

The molecular weight was determined to be 416.

Figure 3:
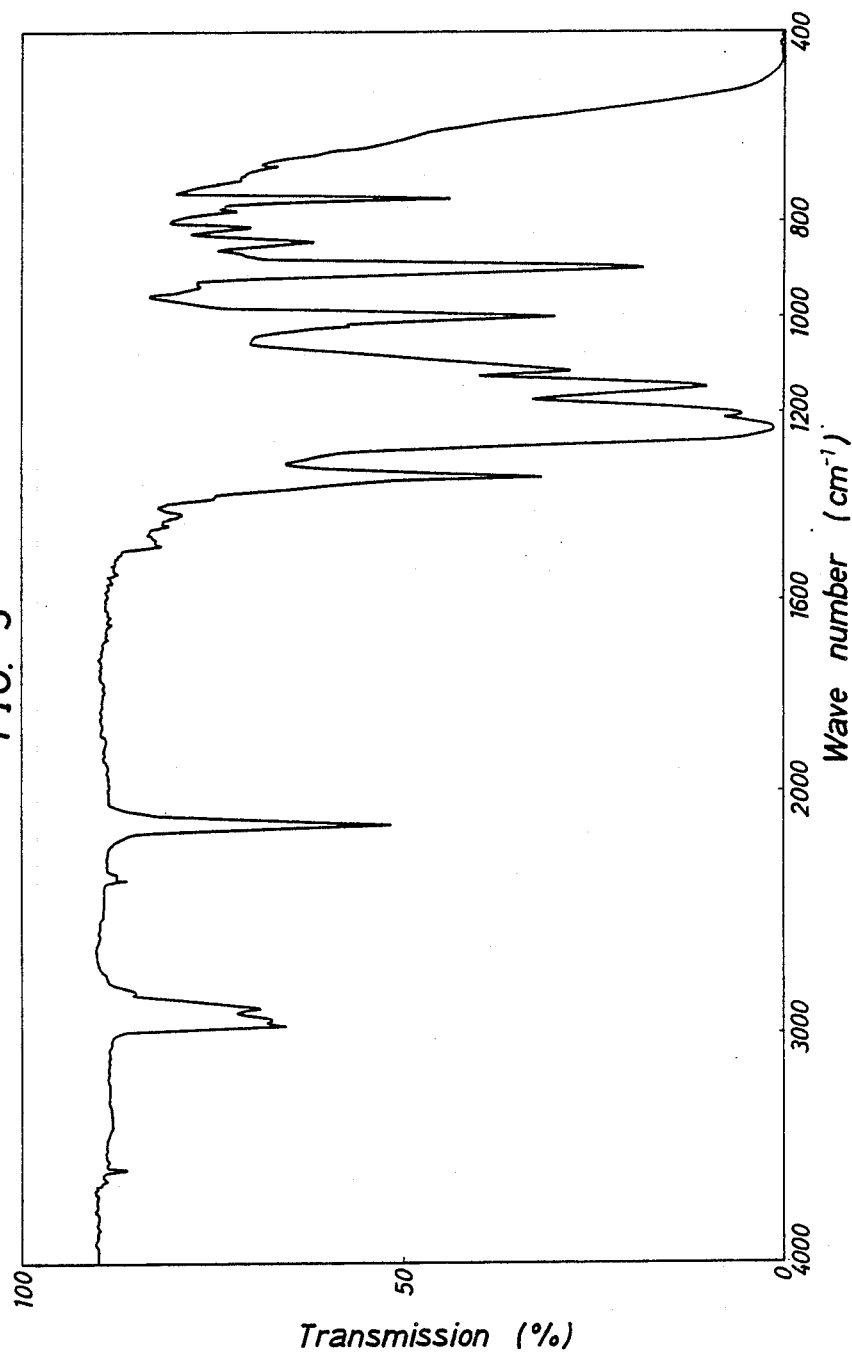

Infrared absorption spectrum. Shown in FIG. 3 A characteristic absorption peak due to Si-H was recognized at a wave number of 2,125cm$^{-1}$. $^1$H-NMR spectrum:

internal standard: benzene.

δ: 3.72 to 4.18ppm (d, 2H, >CF—CH$_2$O),
3.28 to 3.72ppm (t, 2H, —O—CH$_2$—C),
1.32 to 1.98ppm (m, 2H, —O—C—CH$_2$—C),
0.35 to 0.92ppm (m, 2H, —C—CH$_2$Si—),
0.25 to -0.12ppm (d, 6H, Si—CH$_3$)
3.72 to 4.18ppm (m, 1H, Si—H), From the above results, the compound obtained was identified to be 6-trifluoromethyl-6,8,8,9,9,10,10,10-octafluoro-4,7-dioxadecyldimethylsilane represented by the formula below, and its yield was calculated to be 75%:

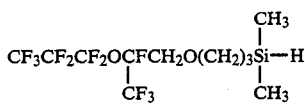

EXAMPLE 4

Procedure in Example 1 was repeated, except that diethyl ether was used in place of tetrahydrofuran; 112 g of 6,9,12-tris(trifluoromethyl)-6,8,8,9,11,11,12,-14,14,15,15,16,16,16-tetradecafluoro-4, was obtained, yield: 75%.

EXAMPLE 5

(1) First step 162g (0.3 mole) of 2-heptadecafluorooctylethyldimethylchlorosilane was added dropwise into a mixed solution containing 100ml of 18% hydrochloric acid and 50ml of methanol. The mixture obtained was heated at 80 to 90° C. with stirring for 3 hours, and an organic layer formed was separated, washed with 150ml of an aqueous 5% NaHCO$_3$ solution and 150ml of a saturated aqueous salt cake solution three times. After dried, the organic solution was distilled under vacuum to give 139g of a fraction with a boiling point of 158 to 162° C./4 mmHg. This was subjected to infrared spectrophotomeric analysis; (it was identified as 1,3-bis(2-heptadecafluorooctyl)ethyl-1,1,3,3-tetramethyldisiloxane. Its yield was 90%. (2) Second step Next, into a 200ml four-necked flask were charged 51g (0.05 mole) of the 1,3-bis(2-heptadecafluorooctyl-)ethyl-1,1,3,3-tetramethyldisiloxane thus obtained, 54g (0.4 mole) of 1,1,3,3-tetramethyldisiloxane and 0.2g of trifluoromethane sulfonic acid, and the mixture was reacted at 50 to 60° C. for 3 hours. The resultant mixture was then washed with 100ml of a saturated aqueous salt cake solution three times. After drying, the resultant mixture was distilled under vacuum to give 45g of a fraction with a boiling point of 82 to 83° C./4 mmHg.

(3) Identification

The fraction obtained was subjected to elemental analysis, measurement of molecular weight by GC-MS analysis, and measurements of infrared absorption spectrum and ¹H-NMR spectrum; the following results were obtained.

| Elemental analysis: | | | |
|---|---|---|---|
| | C | H | Si |
| Calculated* | 29.0 | 3.0 | 9.7 |
| Found | 28.8 | 3.1 | 9.6 |

(*Calculated as $C_{14}H_{17}F_{17}OSi_2$)

GC-MS analysis:
The molecular weight was determined to be 580.

Figure 4:
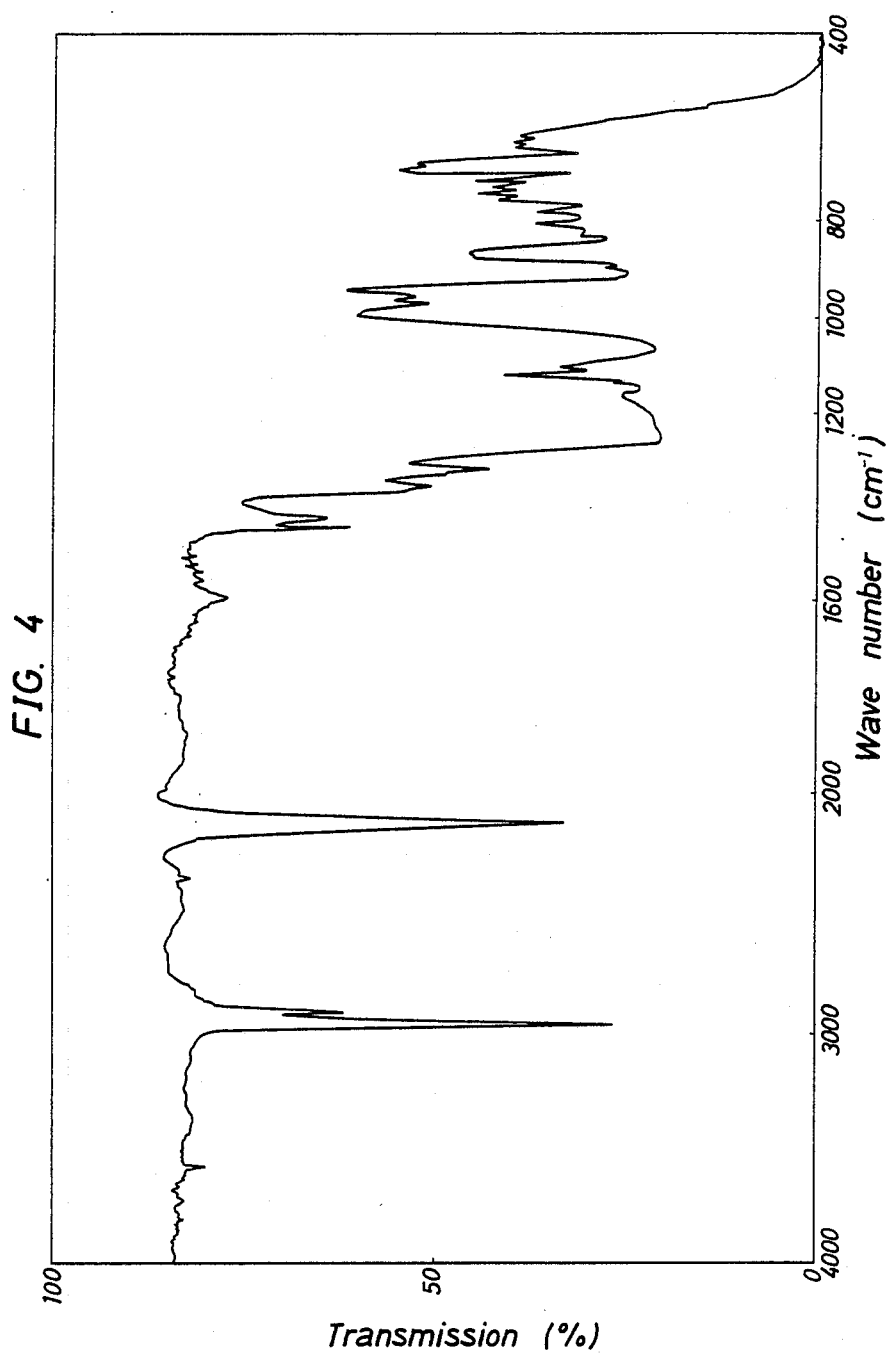

Infrared absorption spectrum: Shown in FIG. 4. A characteristic absorption peak due to Si-H was recognized at a wave number of 2,140cm⁻¹.

¹H-NMR spectrum:
internal standard: benzene,
δ: 2.70 to 1.60ppm (m, 2H, —CF₂—CH₂—C),
1.17 to 0.60ppm (m, 2H, —O—CH₂—Si),
0.25 to 0.17ppm (d, 6H, —O—Si(CH₃)₂—H),
0.20ppm (s, 6H, —C—Si(CH₃)₂OSi),
5.05 to 4.67ppm (m, 1H, Si—H), From the above results, the substance obtained was identified to be 1-bis(2-heptadecafluorooctyl)ethyl-1,1,3,3-tetramethyldisiloxane represented by the formula below, and its yield was calculated to be 78%:

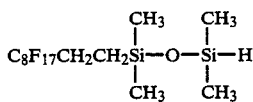

EXAMPLE 6

The procedure of the first step in Example 5 was repeated, except that 132g (0.3 mole) of (2-tridecafluorohexyl)ethyldimethylchlorosilane was used in place of the chlorosilane used in the first step of Example 5.

118g of 1,3-bis(2-tridecafluorohexyl)ethyl-1,1,3,3-tetramethyldisiloxane was obtained as a fraction with a boiling point with 129 to 130° C./4 mmHg. yield: 95%.

Next, following the procedure of the second step of Example 5, 77g (0.093 moles) of the 1,3-bis(2- tridecafluorohexyl)ethyl-1,1,3,3-tetramethyldisiloxane thus obtained and 107g (0.8 moles) of 1,1,3,3-tetramethyldisiloxane were reacted in the presence of 0.5g of trifluoromethane sulfonic acid to give 64g of a fraction with a boiling point of 81 to 82° C./11 mmHg.

The fraction obtained was subjected to elemental analysis, measurement of molecular weight by GC-MS analysis, and measurements of infrared absorption spectrum and ¹H-NMR spectrum; the following results were obtained.

| Elemental analysis: | | | |
|---|---|---|---|
| | C | H | Si |
| Calculated* | 30.0 | 3.6 | 11.7 |
| Found | 29.8 | 3.5 | 11.6 |

(*Calculated as $C_{12}H_{17}F_{13}OSi_2$)

GC-MS analysis:
The molecular weight was determined to be 480.

Figure 5:
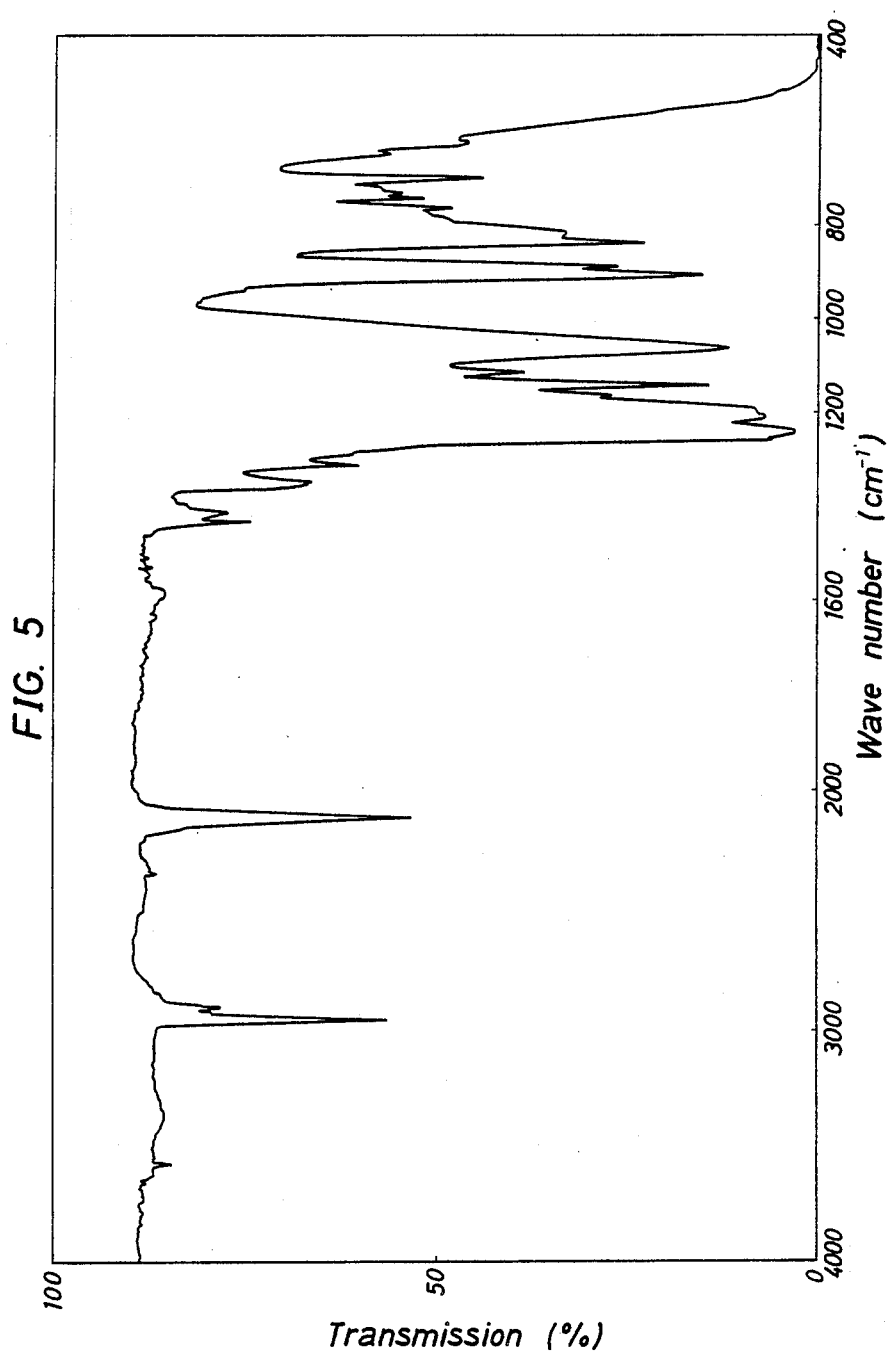

Infrared absorption spectrum: Shown in FIG. 5. A characteristic absorption peak due to Si-H was recognized at a wave number of 2,140cm⁻¹.

¹H-NMR spectrum:
internal standard: benzene.
δ: 2.68 to 1.65ppm (m, 2H, —CF₂—CH₂—C),
1.12 to 0.60ppm (m, 2H, —O—CH₂—Si), 0.23 to 0.17ppm (d, 6H, —O—Si(CH₃)₂—H),
0 20ppm (s, 6H, —C—Si(CH₃)₂OSi),
5.00 to 4.65ppm (m, 1H, Si—H), From the above results, the substance obtained was identified to be 1-(2-tridecafluorohexyl)ethyl-1,1,3,3-tetramethyldisiloxane represented by the formula below, and its yield was calculated to be 72%:

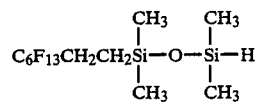

EXAMPLE 7

The procedure of the first step in Example 5 was repeated, except that 136g (0.4 mole) of (2-nonafluorobutyl)ethyldimethylchlorosilane was used in place of the chlorosilane used in the first step of Example 5. 65g of 1,3-bis(2-nonafluorobutylethyl)-1,1,3,3-tetramethyldisiloxane was obtained as a fraction with a boiling point of 96 to 97° C./4 mmHg. Yield: 85%.

Next, following the procedure of the second step of Example 5, 63g (0.1 mole) of 1,3-bis(2-nonafluorobutylethyl)-1,1,3,3-tetramethyldisiloxane and 107g mole) to 1.1.3.3-tetramethyldisiloxane were reacted in the presence of 0.3g of trifluoromethane sulfonic acid to give 54g of a fraction with a boiling point of 65° C./20 mmHg.

The fraction obtained was subjected to elemental analysis and measurement of molecular weight by GC-MS analysis, and measurements of infrared absorption spectrum and ¹H-NMR spectrum; the following results were obtained.

| Elemental analysis: | | | |
|---|---|---|---|
| | C | H | Si |
| Calculated* | 31.6 | 4.5 | 14.8 |
| Found | 31.6 | 4.3 | 14.7 |

(*Calculated as $C_{10}H_{17}F_9OSi_2$)

GC-MS analysis:
The molecular weight was determined to be 380.

Figure 6:
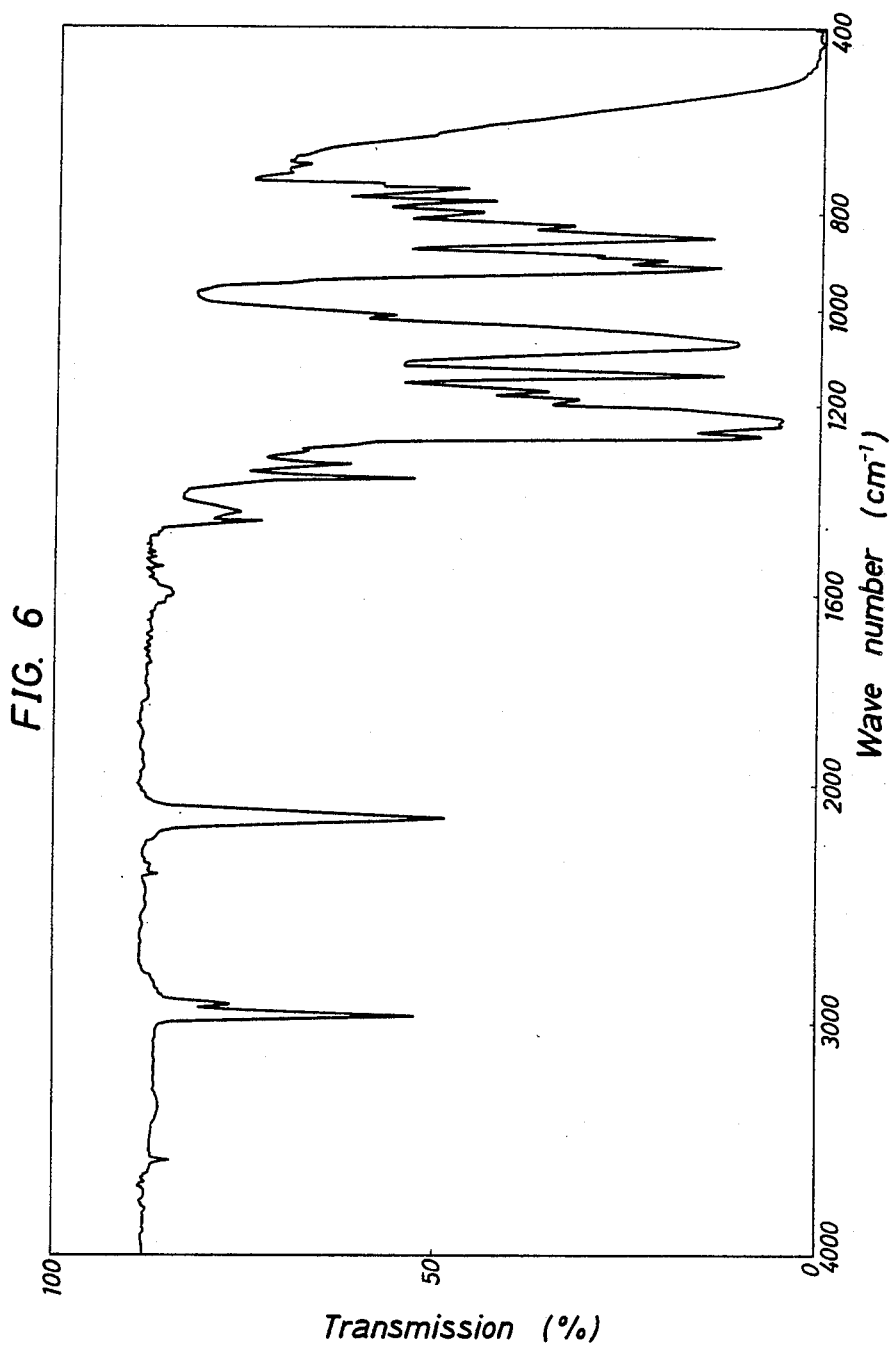

Infrared absorption spectrum: Shown in FIG. 6. A characteristic absorption peak due to Si-H was recognized at a wave number of 2,140.⁻¹ cm.

¹H-NMR spectrum:
internal standard: benzene.
δ: 2.70 to 1.65ppm (m, 2H, —CF₂—CH₂—C),
1.13 to 0.67ppm (m, 2H, —O—CH₂—Si),
0.30 to 0.23ppm (d, 6H, —O—Si(CH₃)₂—H)
0.25ppm (s, 6H, —C—Si(CH₃)₂OSi),
5.02 to 4.68ppm (m, 1H, Si—H), From the above results, the substance obtained was identified to be 1-(2-nonafluorobutyl)ethyl-1,1,3,3-tetramethyldisiloxane represented by the formula below, and its yield was calculated to be 71%:

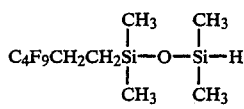

EXAMPLE 8

In a 300ml four-necked flask were charged 103g (0.15 mole) of 6,9,12-tris(trifluoromethyl)-6,8,8,9,11,11,-12,14,14,15,15,16,16,16-tetradecafluoro-4,7,10,13-tetraoxahexadecene-1, 34g (0.25 mole) of 1,1,3,3-tetramethyldisiloxane and 1g of an n-butanol solution of chloroplatinic acid (platinum content: 1% by weight), and the mixture was refluxed under heating for 20 hours. After completion of the reaction, the reaction mixture was distilled under vacuum to give 33g of a fraction with a boiling point of 112 to 115° C./3 mmHg.

The fraction obtained was subjected to elemental analysis, measurement of molecular weight by GC-MS analysis, measurements of infrared absorption spectrum and $^1$H-NMR spectrum; the following results were obtained.

| | Elemental analysis: | | |
|---|---|---|---|
| | C | H | Si |
| Calculated* | 27.8 | 2.6 | 6.8 |
| Found | 28.0 | 2.5 | 6.8 |

(*Calculated as $C_{19}H_{21}F_{23}O_5Si_2$)

Figure 7:
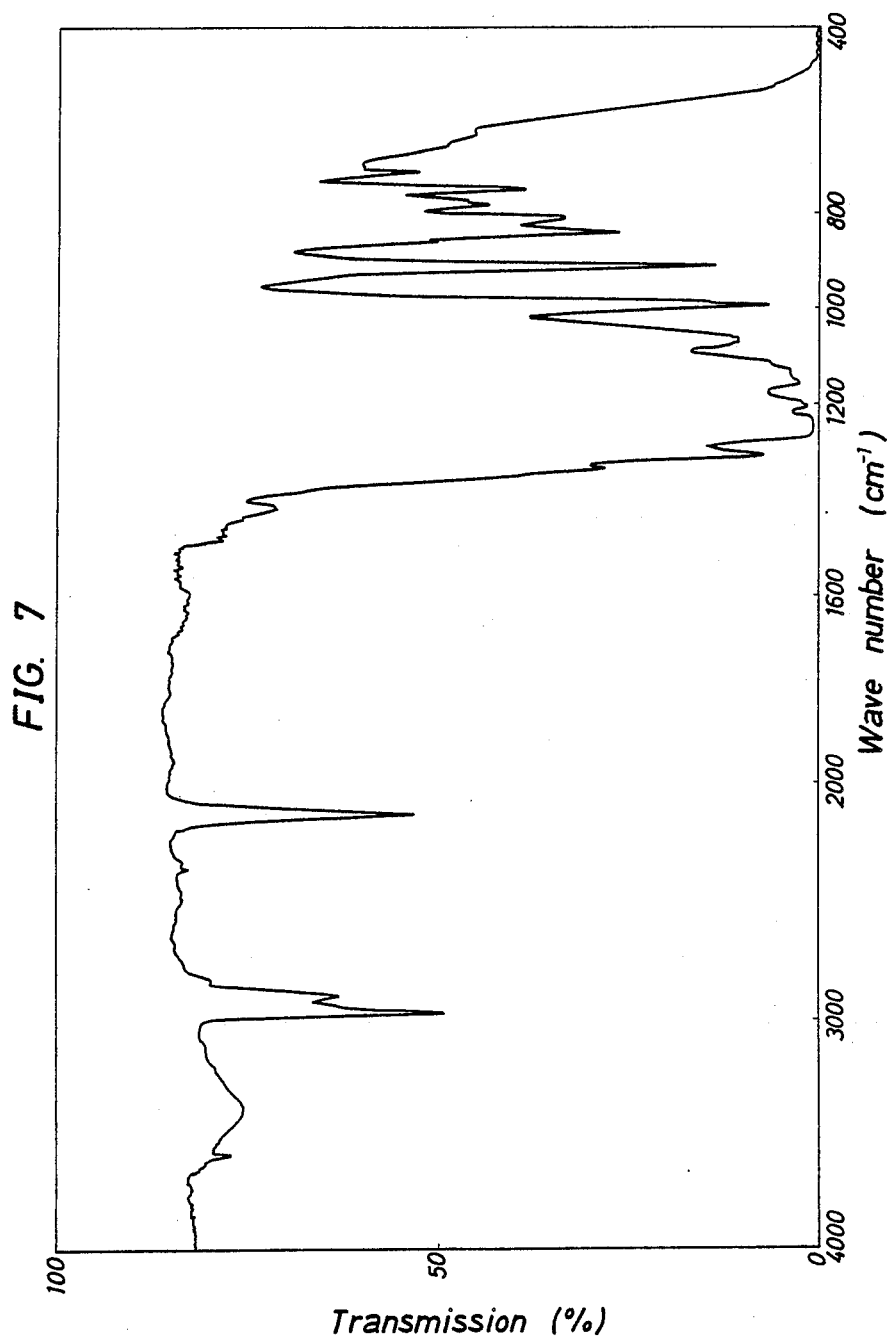

GC-MS analysis:
The molecular weight was determined to be 822.
Infrared absorption spectrum: Shown in FIG. 7. A characteristic absorption peak due to Si-H was recognized at a wave number of 2,130cm$^{-1}$. $^1$H-NMR spectrum:
internal standard: benzene.
δ: 3.77 to 4.17ppm (d, 2H, >CF—CH$_2$O),
3.30 to 3.77ppm (t, 2H, —O—CH$_2$—C),
1.35 to 1.96ppm (m, 2H, —O—C—CH$_2$—C),
0 30 to 0.80ppm (m, 2H, —C—CH$_2$Si—),
0.10ppm (s, 6H, —C—Si(CH$_3$)$_2$OSi),
0.13 to 0.15ppm (d, 6H, —O—Si(CH$_3$)$_2$—H),
4.57 to 5.03ppm (m, 1H, Si—H), From the above results, the substance obtained was identified to be 1- [6,9,12-tris(trifluoromethyl)-6,8,8,9,11,11,12,14,14,15,15,16,16,16-tetradecafluoro-4,7,10,13-tetraoxa] hexadecyl-1,1,3,3-tetramethyldisiloxane represented by the formula below, and its yield was calculated to be 71%:

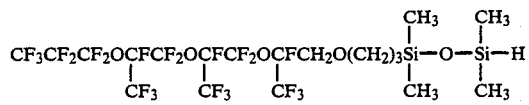

EXAMPLE 9

The procedure of Example 8 was repeated, except that the two reactants used in Example 8 were replaced with 104g (0.2 mole) of 6,9-bis(trifluoromethyl)-6,8,8,9,-11,11,12,12,13,13,13-undecafluoro-4,7,10-trioxatridecene-1 and 40g (0.3 mole) of 1,1,3,3-tetramethyldisiloxane. 66g of a fraction with a boiling point of 100 to 102/5 mmHg was obtained.

The fraction obtained was subjected to elemental analysis, measurement of molecular weight by GC-MS analysis, and measurements of infrared absorption spectrum and $^1$H-NMR spectrum; the following results were obtained.

| | Elemental analysis: | | |
|---|---|---|---|
| | C | H | Si |
| Calculated* | 29.3 | 3.2 | 8.6 |
| Found | 26.5 | 3.3 | 8.5 |

(*Calculated as $C_{15}H_{21}F_{17}O_4Si_2$)

Figure 8:
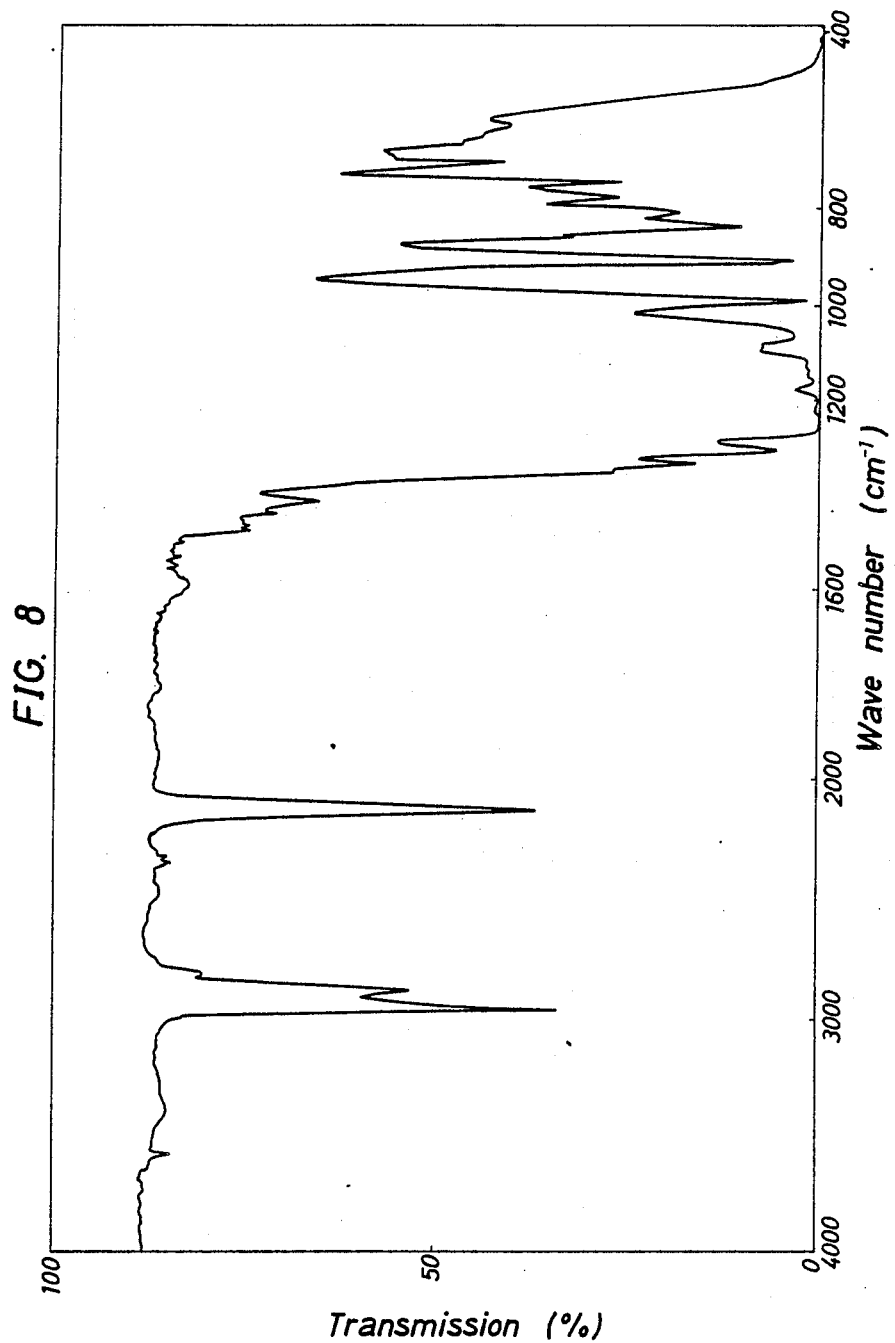

GC-MS analysis:
The molecular weight was determined to be 656.
Infrared absorption spectrum: Shown in FIG. 8. A characteristic absorption peak due to Si-H was recognized at a wave number of 2,130cm$^{-1}$.
$^1$H-NMR spectrum:
internal standard: benzene.
δ: 3.70 to 4.13ppm (d, 2H, >CF—CH$_2$O),
3.30 to 3.73ppm (t, 2H, —O—CH$_2$—C),
1.30 to 2.00ppm (m, 2H, —O—C—CH$_2$—C),
0.37 to 0.87ppm (m, 2H, —C—CH$_2$Si—),
0.08ppm (s. 6H, —C—Si(CH$_3$)$_2$OSi),
13 to 0.18ppm (d, 6H, —O—Si(CH$_3$)$_2$—H),
4.57 to 5.03ppm (m, 1H, Si—H), From the above results, the substance obtained was identified to be 1- [6,9,-bis(trifluoromethyl)-6,8,8,9,11,11,12,12,13,13,13-undecafluoro-4,7,10-trioxa]-tridecyl -1,1,3,3-tetramethyldisiloxane represented by the formula below, and its yield was calculated to be 50%:

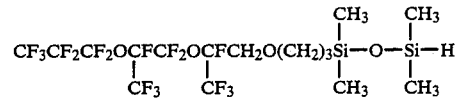

EXAMPLE 10

Following the procedure in Example 8, 74g of a fraction with a boiling point of 73 to 75° C. /5 mmHg was obtained from 178g (0.5 moles) of 6-trifluoromethyl-6,8,8,9,9,10,10,10-octafluoro-4,7-dioxadecene-1 and 201g (1.5 moles) of 1,1,3,3-tetramethyldisiloxane. (Yield: 30%)

The fraction obtained was subjected to elemental analysis, measurement of molecular weight by GC-MS analysis, and measurements of infrared absorption spectrum and $^1$H-NMR spectrum; the following results were obtained.

| | Elemental analysis: | | |
|---|---|---|---|
| | C | H | Si |
| Calculated* | 31.8 | 4.3 | 11.5 |
| Found | 31.9 | 4.3 | 11.6 |

(*Calculated as $C_{13}H_{21}F_{11}O_3Si_2$)

Figure 9:
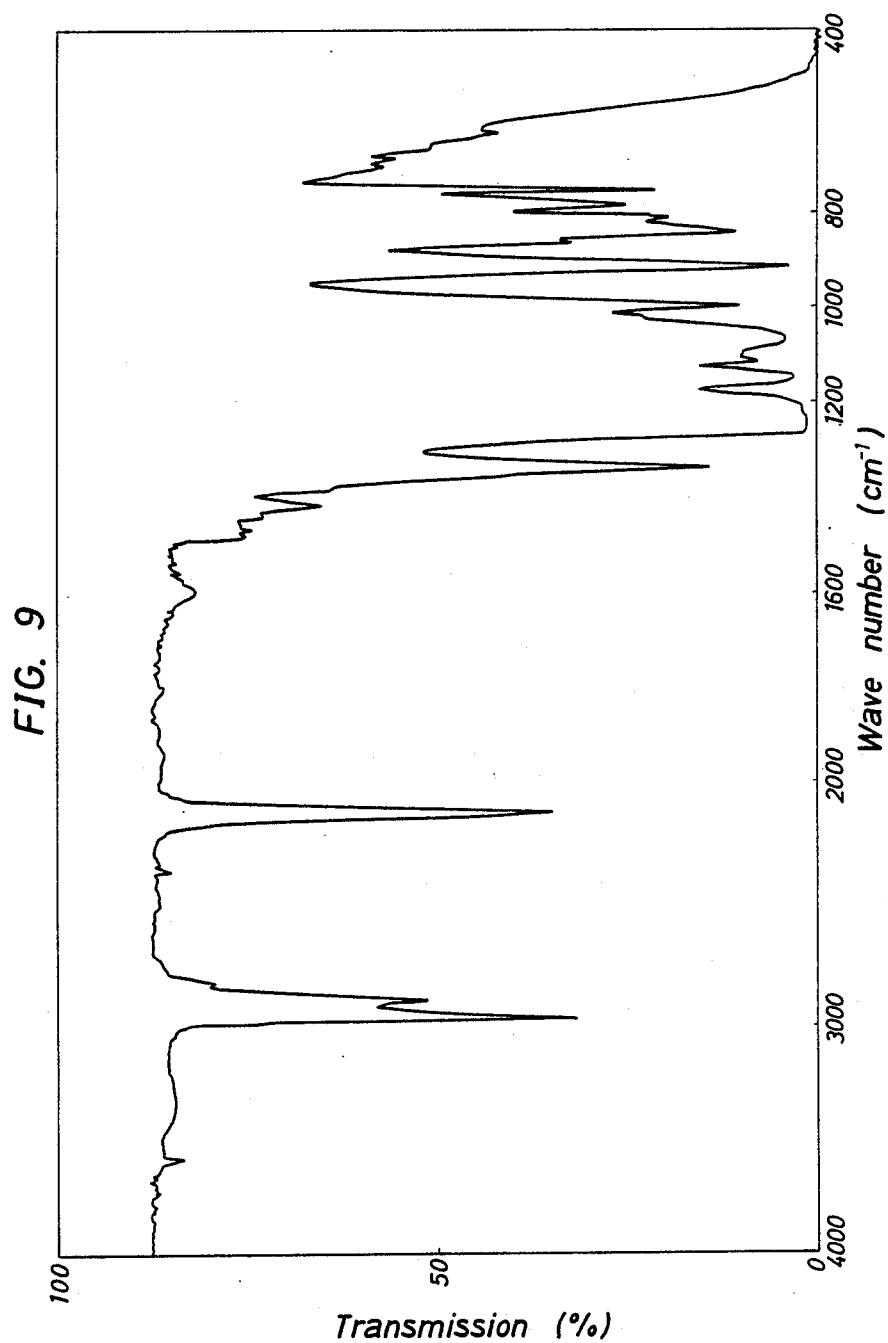

GC-MS analysis:
The molecular weight was determined to be 490.
Infrared absorption spectrum: Shown in FIG. 9. A characteristic absorption peak due to Si-H was recognized at a wave number of 2,130cm$^{-1}$.
$^1$H-NMR spectrum:
internal standard: benzene.
δ:3.73 to 4.17ppm (d, 2H, >CF—CH$_2$O),
3.30 to 3.70ppm (t, 2H, —O—CH$_2$—C),
1.30 to 2.00ppm (m, 2H, —O—C—CH$_2$—C), 0.33 to 0.83ppm (m, 2H, —C—CH$_2$Si),
0.08ppm (s, 6H, —C—Si(CH$_3$)$_2$OSi),
0.12 to 0.17ppm (d, 6H, —SiO—Si(CH$_3$)$_2$—H),
4.60 to 5.03ppm (m, 1H, Si—H), From the above results, the substance obtained was identified to be 1- [6-trifluoromethyl-6,8,8,9,9,10,-10,10-octafluoro-4,7-dioxa]decyl-1,1,3,3, tetramethyldisiloxane represented by the following formula:

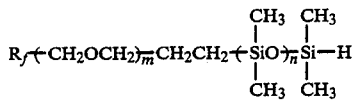

We claim:

1. A fluorine-containing organosilicon compound represented by the following general formula (I):

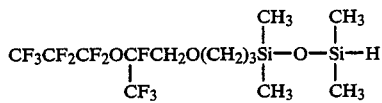

(I)

wherein R$_f$ represents a perfluoroalkyl group or a perfluoroalkyl ether group, and m and n are each an integer of 0 or 1.

2. The fluorine-containing organosilicon compound according to claim 1, wherein R$_f$ in the general formula (I) is a perfluoroalkyl group having 4 to 10 carbon atoms.

3. The fluorine-containing organosilicon compound according to claim 2 which is represented by the following general formula (Ia)

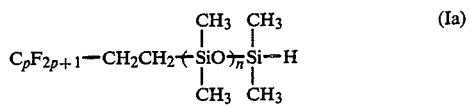

(Ia)

wherein, p is an integer of 4 to 10, and n is the same as defined above.

4. The fluorine-containing organosilicon compound according to claim 1, wherein R, in the general formula (I) is represented by the following formula (II):

(II)

where s is an integer of 1 to 4.

5. A fluorine-containing organosilicon compound according to claim 4 which is represented by the following general formula (Ib):

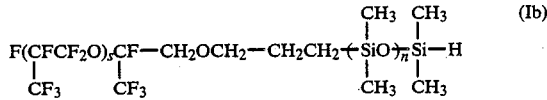

(Ib)

wherein s and n are the same as defined above.

* * * * *

UNITED STATES PATENT AND TRADEMARK OFFICE
CERTIFICATE OF CORRECTION

PATENT NO. : 4,968,828
DATED : Nov. 6, 1990
INVENTOR(S) : Yamamoto

It is certified that error appears in the above—identified patent and that said Letters Patent is hereby corrected as shown below:

On the title page:
Appl. No. 424,533 appearing at [21] on page 1, column 1, should read --Appl. No. 424,553--.

Signed and Sealed this

Twenty-sixth Day of January, 1993

Attest:

STEPHEN G. KUNIN

*Attesting Officer*   *Acting Commissioner of Patents and Trademarks*